United States Patent
Gleim (10) Patent No.: US 11,090,504 B2
(45) Date of Patent: Aug. 17, 2021

(54) DEVICE FOR INFLUENCING BIOLOGICAL PROCESSES IN LIVING TISSUE

(71) Applicant: BEMER INT. AG, Triesen (LI)

(72) Inventor: Peter Gleim, Triesen (LI)

(73) Assignee: Bemer Int. AG, Triesen (LI)

( * ) Notice: Subject to any disclaimer, the term of this patent is extended or adjusted under 35 U.S.C. 154(b) by 98 days.

(21) Appl. No.: 16/463,734

(22) PCT Filed: Jul. 21, 2017

(86) PCT No.: PCT/EP2017/068498
§ 371 (c)(1),
(2) Date: May 23, 2019

(87) PCT Pub. No.: WO2018/095589
PCT Pub. Date: May 31, 2018

(65) Prior Publication Data
US 2019/0381331 A1    Dec. 19, 2019

(30) Foreign Application Priority Data
Nov. 24, 2016   (DE) ................... 10 2016 122 691.2

(51) Int. Cl.
*A61N 2/02*        (2006.01)
(52) U.S. Cl.
CPC ........................ *A61N 2/02* (2013.01)
(58) Field of Classification Search
CPC ............ E04H 17/20; A61N 2/004; A61N 2/02
USPC ...................................................... 600/9–15
See application file for complete search history.

(56) References Cited

U.S. PATENT DOCUMENTS

| 4,428,366 A | 1/1984 | Findl et al. |
| 5,181,902 A | 1/1993 | Erickson et al. |
| 5,480,373 A * | 1/1996 | Fischer ............... A61N 2/02 600/14 |
| 5,877,627 A | 3/1999 | Fischer et al. |

(Continued)

FOREIGN PATENT DOCUMENTS

| DE | 42 21 739 A1 | 1/1993 |
| EP | 0 266 807 A2 | 5/1988 |

(Continued)

OTHER PUBLICATIONS

EP2050481A1 English Translation, Kafka, Wolf A (Year: 2009).*

(Continued)

*Primary Examiner* — Navin Natnithithadha
*Assistant Examiner* — Sunita Reddy
(74) *Attorney, Agent, or Firm* — Henry M. Feiereisen LLC (57) ABSTRACT

A device for influencing biological sequences in living tissue, in particular a human body, includes a field generation device for generating the pulsating magnetic field to be applied to at least a part of the tissue, and a pulse generator controlling the field generation device. The pulsating magnetic field is composed of a sequence of primary pulses which are formed by a plurality of superimposed sub-pulses, the pulse repetition rate of which is between 0.01 and 1000 Hz. The sequence of primary pulses separated is from a second sequence of primary pulses by a rest phase. The curve profile of the maximum amplitude of the primary pulses has a slope mB of $-\infty < mB < -0.1$ at the beginning of the rest phase and/or has a slope mE of $\infty > mE > 0.1$ at the end of the rest phase.

12 Claims, 6 Drawing Sheets

(56) References Cited

U.S. PATENT DOCUMENTS

| | | | | |
|---|---|---|---|---|
| 2004/0230224 | A1* | 11/2004 | Gordon | A61N 2/02 607/2 |
| 2010/0057146 | A1* | 3/2010 | Gleim | A61N 2/02 607/1 |
| 2011/0125203 | A1* | 5/2011 | Simon | A61N 1/40 607/2 |
| 2011/0263925 | A1* | 10/2011 | Bratton | A61N 2/02 600/14 |
| 2012/0209055 | A1* | 8/2012 | Gleim | A61N 2/02 600/14 |
| 2014/0046116 | A1* | 2/2014 | Gleim | A61N 2/02 600/14 |
| 2014/0371515 | A1* | 12/2014 | John | A61N 2/02 600/13 |
| 2016/0008620 | A1* | 1/2016 | Stubbeman | A61N 1/36082 600/14 |

FOREIGN PATENT DOCUMENTS

| | | |
|---|---|---|
| EP | 0 266 907 A2 | 5/1988 |
| EP | 0 377 284 A2 | 7/1990 |
| EP | 0 594 655 B1 | 3/1996 |
| EP | 0 729 318 B1 | 5/1997 |
| EP | 0 995 463 B1 | 8/2001 |
| EP | 1 364 679 A2 | 11/2003 |
| EP | 2 050 481 A1 | 4/2009 |
| WO | WO 96/32159 A1 | 10/1996 |
| WO | WO 2011/023634 A1 | 3/2011 |
| WO | WO 20110023634 A1 | 3/2011 |

OTHER PUBLICATIONS

International Search Report issued by the European Patent Office in International Application PCT/EP2017/068498 dated Oct. 27, 2017.
K. Spodaryk: "Red blood metabolism and haemoglobin oxygen affinity: effect of electromagnetic fields on healthy adults", in: Int. World Congress Bio-Electro-Magnetic-Energy Regulation, 2001, pp. 15-19.
Kafka WA Spodaryk K (2003) Effects of extremely weak BEMER 3000 type pulsed electromagnetic fields on red metabolism and hemoglobin oxygen affinity, In: Fizoterapia 11 (3): pp. 24-31.
R. Klopp: "Vitalmikroskopische und reflexionsspektrometrische Untersuchungen zur Wirkung des Gerätesystems "Bermer 3000" auf den Funktionszustand der Mikrozirkulation", In: Institut für Mikrozorkulation, 2004.
R. Klopp et al: Einfluss eines pulsierenden elektromagnetischen Feldes mit vasomotorischer Stimulation auf einen eingeschränkten Funktionszustand der Mikrozirkulation, Komplment. Integr. Med Aug. 2007: pp. 47-53.
R. Jelinek,et al: "The electromagnetic BEMER 3000 signal modifies response to teratogens", in: . 3rd Int. World Congress Bio-Electro-Magnetic Energy-Regulation, Bad-Windsheim,Germany, Emphyspace 3, 2002.
M. Preissinger: 'Verbesserte Wundheilung lurch gekoppelte, BEMER 3000 typisch gepulste, Elektromagnetfeld- und LED-Licht-Thorapie am Beispiel vergleichender Untersuchungen an standardisierten Wunden nach Ovariektomie bei Katzen (felidae)', in: . Edwin Ganster (Hrsg) Österreichische Gesellschaft der Tierärzte (ÖGT) Kleinitertage-Dermatologie, Mar. 2002, Salzburg Congress.
K. Spodaryk: "The effect of extremely weak electromagnetic field treatments upon signs and symptoms of delayed onset of muscle soreness: A placebo controlled clinical double blind study", in: Medicine Saortiva 6, 2002, pp. 19-25.
R. Klopp et al.: Magnetfeldtherapie: Komplementär-therapeutisch sinnvoll oder Unsinn? Stellungsnahme unter Berücksichtigung neuer Forschungsergebnisse mit dem Gerätesystem BEMER 3000, Institut für Mikrozirkulation, Berlin, 2005.
K. Spodaryk et al.: "The influence of extremely weak BEMER 3000 typed pulsed electromagnetic fields on ratings of perceived exertion at ventilatory threshold", in: Marincek et al (eds) Rehabilitation Sciences in the New Millennium Challenge for Multidisciplinary Research. $8^{th}$ Congress of EFRR, Ljubljana. Medimont International Proceedings, 2004, pp. 279-283.
B. Rihova : "Die Wirkung der elektomagnetischen Felder des BEMER 3000 auf das Wachstum des experimentellen Mäuse-EL 4T Zellen-Lymphoms", in: SAMET Kongress, Interlaken, 2004.
Kafka et al.: "Application of extreme frequent (BEMER type) pulsed electromaenetic fields in orthopedics", in Orthopädische Praxis 41 (1): 2005, 22-24.
Walther et al: "Effects of weak, low frequency pulsed electromagnetic fields (BEMER type) on gene expression of human mesenchymal stem cells and chondrocytes: an In virtro study", in: Electromagnetic Biology and Medicine, Manuscript ID: 257936, 2007.
Michels-Wakili et al: "BEMER 3000 pulsed low-energy electromagnetic fields reduce dental anxiety: a randomized placebo controlled single-blind study", in: . $10^{th}$ International Congress on Modern Pain Control, Jun. 5-8, 2003 Edinburgh, GB.
Bematzky et al.: Auswirkung von speziellen, (BEMER-typisch) gepusten elektro-magnetischen Feldern auf Schlafqualitat und chronischen Kreuzschmerz des Stütz-und Bewegunsapparates (low back pain): Eine doppelblinde randomisierte Duo Center Studie (Der Schmerz, published), 2007.
M. Gabrys: Pulsierende Magnetfeldtherapie bei zytostatisch bedingter Polyneuropathie. Deutsche Zeitschrift für Onkologie 36, 2004, pp. 154-156.
Carpenter et al: "Biological effects of electric and magnetic elds: sources and mechanism, vol. 1. Beneficial and harmful effects. vol. 2", in: Academic Press, 1994.
W Bohn et al: Energie and Gesundheit: BEMER 3000 Bio-Elektro-Magnetische-Energie-Regulation nach; Prof. Dr. Wolf A. Kafka. Haug Verlag, Stuttgart (Thieme Verlagsgruppe): 2004, pp. 1-130.
WA Kafka: "The BEMER 3000 Therapy: A new complemntary "electro-magnetic drug" effectively supports widespread scattered prophylactic and therapeutic treatments", in: Kochueva E (ed) Achievments in space medicine into health care practice and industry $3^{rd}$ European praxis matured congress Kopie-Druck sponsored by ESA, DLR % POCKO MOC; 2006.
M. Quittan et al.: "Klinische Wirksamkeiten der Magnetfeldtherapie-eine Literaturübersicht", in: Acta Medica Austriaca 3, 2000, pp. 61-68.
Matthes Rudiger; "Guidance on determining compliances of exposure to pulsed and complex non sinusoidal waveforms below 100khz with ICNIRP Guidelines", in: The International Commission on Non-Ionizing Radiation Protection ICNIRP Secretariat, Federal Office of Radiation Protection, Institute for Radiation Hygene], 2003.

\* cited by examiner

DEVICE FOR INFLUENCING BIOLOGICAL PROCESSES IN LIVING TISSUE

CROSS-REFERENCES TO RELATED APPLICATIONS

This application is the U.S. National Stage of International Application No. PCT/EP2017/068498, filed Jul. 21, 2017, which designated the United States and has been published as International Publication No. WO 2018/095589 and which claims the priority of German Patent Application, Serial No. 10 2016 122 691.2, filed Nov. 24, 2016, pursuant to 35 U.S.C. 119(x) (d).

BACKGROUND OF THE INVENTION

The invention relates to a device and an electric or electromagnetic signal for influencing biological processes in living tissue, in particular a human body, by applying a pulsating electromagnetic field to at least a part of the tissue.

Devices which generate electromagnetic fields and which are routinely used for therapeutic purposes in hospitals, especially in the field of orthopedics, have been known since the beginning of the 70 s. The sinusoidal magnetic fields, which were used in semi-invasive methods with pulsating magnetic fields, had a frequency of 2 to 20 Hz and magnetic flux densities between 1 mT and 10 mT. An alternating voltage for generating an external magnetic field was induced at implanted electrodes with the aid of a so-called secondary element.

Furthermore, however, noninvasive treatment without secondary element was also known, in which only very weak electrical currents were induced in the treated body part, which had to be located in the center of the coil. Devices for whole body treatment have also been known since the 70 s, in which the field lines are distributed uniformly in the body.

In these treatment forms, a generator is used in this case for actuating a magnetic field generation device, in which the generator actuates the magnetic field generation device such that the magnetic field consists of a plurality of base pulses or primary pulses which have characteristic forms in the time interval and amplitude curve thereof. The pulse frequency is typically between 0 and 1000 Hz. Such a primary pulse can have sinusoidal, trapezoidal, or also sawtooth form (EP 0 594 655 B1 (König Herbert), EP 0 729 318 B1 (Fischer Gerhard, EP-A-0 377 284) or, as in EP 0 995 463 B1 (Kafka Wolf A) can have a sinusoidal modulated field intensity curve which rises exponentially on average, having magnetic flux densities in the range from nanoTesla to several milliTesla. Furthermore, the primary pulses can be composed of a series of chronologically successive sub-pulses, which differ in the amplitudes and/or rising or falling slopes thereof, and thus finally also in the individual duration thereof (cf. EP 0 995 463 B1).

The magnetic fields are frequently generated by one or more electric coils, which are actuated independently of one another (EP 1 364 679 A2, EP-A 0 266 807, EP-A-0 266 907, DE-A 4 221 739. U.S. Pat. No. 5,181,902, WO-A-96/32159, U.S. Pat. No. 4,428,366, EP 0 995 463 B1). Presently, the therapeutic application is typically performed noninvasively for reasons of operative expenditure and the risks linked thereto.

According to common belief, the influence on the biological system is based on a still unknown cooperation of energy components of the magnetic and electrical field components generated by the devices. The physiological and biological interactions triggered by the applied electrical and magnetic field are accordingly based on energetic activation of the reactivity of molecular structures, the naturally provided regulation mechanisms directed to self-preservation. The energetic activation can be triggered directly, magnetically and/or according to the principle of induction (Maxwell equations), and indirectly, by electrical force actions. In contrast, the molecular structures can have ionic, atomic, and molecular form.

For example, EP 0 995 463 B1, describes that an electromagnetic field results in a significant activation of an array of differentiated physical-physiological processes in relation to biological objects to which it is not applied. Thus, for example, The formation of high-energy compounds, in particular of adenosine triphosphate (ATP) and bis-2-3-phospoglycerate (BPG) were observed in human erythrocytes [Spodaryk K (2001) Red blood metabolism and haemoglobin oxygen affinity: effect of electromagnetic fields on healthy adults. In: Kafka W A (ed) 2nd Int World Congress Bio-Electro-Magnetic-Energy-Regulation. Emphyspace 2: 15-19; Kafka W A, Spodaryk K (2003) Effects of extremely weak BEMER 3000 type pulsed electromagnetic fields on red blood metabolism and hemoglobin oxygen affinity. Fizoterapia 11 (3): 24-31].

The improvement of the functional state of the microcirculation, in particular with respect to the circulation behavior (particularly also in the case of diabetes-related circulation illnesses) and the oxygen utilization [Klopp R (2004) Vitalmikroskopische und reflexionsspektrometrische Untersuchungen zur Wirkung des Gerstesystems "BEMER 3000" auf den Funktionszustand der Mikrozirkulation [vital microscopic and reflection-spectrometric studies on the effect of the device system "BEMER 3000" on the functional state of the microcirculation]. Report from the Institut für Mikrozirkulation, Berlin; Klopp R, Niemer W (2007) Einfluss eines pulsierenden elektromagnetischen Feldes mit vasomotorischer Stimulation auf einen eingeschrankten Funktionszustand der Mikrozirkulation [influence of a pulsating electromagnetic field with vasomotor stimulation on a restricted functional state of the microcirculation]. Komplement. Integr. Med August/2007: 47-53].

The acceleration of the process of protective mechanisms, in particular with respect to an accelerated process described in Klopp 2004 of leukocyte immune defense reactions triggered by infection and supported by complex interaction of signal and adhesion molecules.

The protection against chemical stress factors, in particular the reduction of chemically induced (by the teratogen cyclophosphamide) malformations in the ontogenesis of warm-blooded vertebrate embryos (on the model of chicken eggs) [Jelínek R, Bláha J, Dbalý Jaroslav (2002) The electromagnetic BEMER 3000 signal modifies response to teratogens. In: Kafka W A (ed) 3nd Int. World Congress Bio-Electro-Magnetic Energy-Regulation, Bad-Windsheim, Germany, Emphyspace 3].

The improved healing of standard produced wounds [Kafka W A, Preilßinger M (2002) Verbesserte Wundheilung durch gekoppelte, BEMER 3000 typisch gepulste, Elektromagnetfeld- und LED-Ucht-Therapie am Beispiel vergleichender Untersuchungen an standardisierten Wunden nach Ovariektomie bei Katzen (felidae) [improved wound healing by coupled, BEMER 3000 typical pulsed electromagnetic field and LED light therapy on the example of comparative experiments on standardized wounds after ovariectomy in cats (Felidae)]. In: Edwin Ganster (Hrsg) Österrelchische Geselschaft der Tierirzte (ÖGT) Kleintiertage-Dermatologie 2-3 Mar. 2002, Salzburg Congress]

Antioxidative regulations in particular with respect to enzymatically and spectrophotometrically determined accelerated reduction conversion rates [Spodaryk K (2002) The effect of extremely weak electromagnetic field treatments upon signs and symptoms of delayed onset of muscle soreness: A placebo controlled clinical double blind study. Medicina Sportiva 6: 19-25; Klopp R, Niemer W, Pomrenke P, Schulz J (2005) Magnetfeldtherapie: Kompementär-therapeutisch sinnvoll oder Unsinn? Stellungnahme unter Bercksichtigung neuer Forschungsergebnisse mit dem Geratesystem BEMER 3000 [magnetic field therapy: reasonable for complementary therapy or nonsense? Opinion in consideration of new research results with the device system BEMER 3000], Institut für Mikrozirkulatlon, Berlin]

Increasing performance in elite level sports [Spodaryk K and Kafka W A (2004) The Influence of extremely weak BEMER3000 typed pulsed electromagnetic fields on ratings of perceived exertion at ventilatory threshold. In: Marincek C, Burger H (eds) Rehabilitation Sciences in the New Millennium Challenge for Multidisciplinary Research. 8th Congress of EFRR, Ljubljana. Medimont International Proceedings: 279-283]

Of replication and proliferation mechanisms in particular with respect to a significant reduction of the tumor growth in thymus-free but not in comparatively studied normal mice [Rihova B (2004) Die Wirkung der elektromagnetischen Felder des BEMER 3000 auf das Wachstum des experimentellen Mäuse-EL 4T Zellen-Lymphoms] [the effect of the electromagnetic fields of the BEMER 3000 on the growth of the experimental mouse-EL 4T cell lymphoma], SAMET Kongress, Interlaken; Rihova B, Dbaly J, Kafka W A Exposure to special (BEMER-type) pulsed weak electromagnetic fields does not accelerate the growth of mouse EL4 T cell lymphoma, submissed]

Protein formation and activation in particular with respect to differential up and down regulation of gene-expressed protein quantities. It was possible to show in the scope of a gene chip analysis that the application of the device EP 0 995 463 B1 to stem cells of bone marrow (bone and cartilage cells) Influenced the quantity of the produced proteins differently in relation to untreated: the quantity (expression) of the produced proteins is thus sometimes elevated, sometimes reduced, sometimes it remains uninfluenced (interestingly, inter alia, with respect to the expression of oncogenes) [Kafka W A, Schutze N, Walther M (2005) Einsatz extrem niederfrequent (BEMER typisch) gepulster schwacher elektromagnetischer Felder im Bereich der Orthopädie (Application of extreme low frequent (BEMER type) pulsed electromagnetic fields in orthopedics). Orthopädische Praxis 41 (1): 22-24; Walther M, Meyer F, Kafka W A, Schütze N (2007) Effects of weak, low frequency pulsed electromagnetic fields (BEMER type) on gene expression of human mesenchymal stem cells and chondrocytes: an in vitro study. Electromagnetic Biology and Medicine, Manuscript ID: 257936].

Psychovegetative processes, in particular the reduction of the (dentist) anxiety by an electromagnetic local stimulation of the solar plexus immediately preceding dental treatment [Michels-Wakili S and Kafka W A (2003) BEMER 3000 pulsed low-energy electromagnetic fields reduce dental anxiety: a randomized placebo controlled single-blind study. 10th International Congress on Modern Pain Control 5-8 Jun. 2003 Edinburgh, GB]

The reduction of lumbar-initiated secondary reactions, in particular the reduction of movement pain, sleeplessness, and anxiety [Bematzky G, Kullich W, Aglas F, Ausserwinkler M, Likar R, Pipam W, H. Schwann H, Kafka W A (2007) Auswirkungen von speziellen, (BEMER-typisch) gepulsten elektro-magnetischen Feldem auf SchlafqualitAt und chronischen Kreuzschmerz des Stütz- und Bewegungsapparates (low back pain): Eine doppelblinde randomisierte Duo Center Studie [effects of special (BEMER-typical) pulsed electromagnetic fields on sleep quality and chronic low back pain of the support and movement apparatus (low back pain): a double-blind randomized Duo Center study] (Der Schmerz, in press).

The analgesic effect, in particular with respect to the reduction of polyneuropathy pain states as a result of oxidative stress after chemotherapy [Gabrys M (2004) Pulsierende Magnetfeldtherapie bei zytostatisch bedingter Polyneuropathie (pulsating magnetic field therapy in cytostatically-related polyneuropathy]. Deutsche Zeitschrift für Onkologie 36: 154-156].

have been reported.

Furthermore, in summary, the following have reported on the effects of the application of electromagnetism to biological material Carpenter D O, Aryapetyan S (1994) Biological effects of electric and magnetic fields: sources and mechanism, vol 1. Beneficial and harmful effects, vol 2. Academic Press;

Bohn W, Kafka W A (2004) Energie und Gesundheit: BEMER 3000 Bio-Elektro-Magnetische-Energie-Regulation nach Prof. Dr. Wolf A. Kafka. [energy and health: BEMER 3000 Bio-electromagnetic energy regulation according to Prof. Dr. Wolf A. Kafka] Haug Verlag, Stuttgart (Thieme Verlagsgruppe): 1-130;

Kafka W A (2006) The BEMER 3000 Therapy: A new complementary "electro-magnetic drug" effectively supports widespread scattered prophylactic and therapeutic treatments. In: Kochueva E (ed) Achievements in space medicine into health care practice and industry 3rd European praxis matured congress KOPIE-DRUCK sponsored by ESA, DLR & POCKO MOC];

Quittan M, Schuhfried O, Wiesinger G F, Fialka-Moser V (2000) Klinische Wirksamkeiten der Magnetfeldtherapie—eine Literaturübersicht [clinical efficacies of magnetic field therapy—a literature overview]. Acta Medica Austriaca 3:61-68;

Matthes Rudiger (2003) Guidance on determining compliances of exposure to pulsed and complex non sinusoidal waveforms below 100 khz with ICNIRP GUIDELINES. The International Commission on Non-Ionizing Radiation Protection ICNIRP Secretariat, Bundesamt für Strahlenschutz, Institut fir Strahlenhygiene [federal office of radiation protection, institute for radiation hygiene], Ingolstädter Landstrasse, D-85764 Oberschleissheim, Germany.

As a result of the differentiated effects on tumor growth and gene expression, the effects cannot be explained with improved microcirculation, but rather confirm and imply the assumption specified at the outset, that the electromagnetically induced biological effects are based on the activation of molecular mechanisms having different causes. It is assumed that the different processes therefore require different amounts of energy for the activation thereof. The distribution of the amplitudes, the formation of the flank slopes, and the superposition of the subpulses therefore receive decisive significance, since the intensity distribution over time is characterized by these parameters. The chronological field intensity distributions therefore receive a similar significance as the structure-activity relationship of medication active ingredients in pharmacy.

Since presently only weak-energy devices are used, furthermore harmful side effects are not to be expected. This is confirmed by reports of the WHO [Electromagnetic Fields (EMF) ff. http:/www.who.int/peh-emf/en/; http://www.who.int/topics/electromagnetic_fields/en/;] and a report of a German regulatory authority responsible for the certification of medical products [LGA report 2005], which documented that especially for the device EP 0 995 463 B1—which was estimated to have been used several million times from 1998 to the present according to statistical investigations—no negative health effects were found.

EP 0 995 463 B1 furthermore describes the application of electric or electromagnetic fields to biological material. The application takes place here in two intervals, wherein the frequency of the electric or electromagnetic field in the first interval can differ from the frequency of the electric or electromagnetic field in the second interval. In one described embodiment of EP 0 995 483 B1, the intervals in which electric or electromagnetic fields are applied to the biological material are interrupted by a third interval, in which no application to the biological material takes place, and the amplitude of the electric or electromagnetic field is accordingly equal to 0.

In a refinement described in EP 2 050 481 A1, the intensity curve was adapted over time such that the pulses became more finely adapted to the requirements of the therapy. The optimum shape and sequence of the subpulses individually differs greatly. It is dependent on the type of the tissue subjected to the field, the desired healing success, and the respective individual. The high proportion of the rising or falling flanks sections caused by the plurality of the superimposed subpulses is suspected to have a decisive significance in the stimulation of the exchange processes in the body tissue. Furthermore, EP 2 050 481 A1 describes that two intervals with application of an electromagnetic or electric field to the biological tissue can be interrupted by a pause, in which no application takes place.

However, as a result of the processes, which are not yet completely understood, in the biological tissue subjected to the electromagnetic field, it has not yet been possible to develop an optimized pulse sequence. All previously known devices for treating the human body therefore do not always result in the desired accelerating effect of the healing process. In particular, it is problematic that in previous devices for achieving a significantly accelerated healing success, the application does not operate sufficiently effectively and a treatment has to be carried out with frequent repetitions. This results in elevated stress of the patient and in significantly higher treatment costs as a result.

It is the object of the invention to provide an Improved device and an improved electrical or electromagnetic signal in relation to the prior art, using which more rapid influence, in particular excitation, which is broader in its physiological effect, of biological processes is enabled, by addressing a broad band of electromagnetically activatable molecular structures and thus ensuring a broader physiological breadth of action. The invention is thus directed to the broadest possible effective energetic assistance of the complex interconnected molecular regulation processes. The accompanying therapy concept is thus preventive and is directed to regeneration, preservation, and well-being.

SUMMARY OF THE INVENTION

This object is achieved according to the invention by a device which comprises a pulse generator and a field generation device for generating a pulsating electromagnetic field. The pulse generator is used to actuate the field generation device, wherein the pulse generator actuates the field generation device via suitable current-voltage sequences in such a way that the pulsating electrical or electromagnetic field consists of a plurality of primary pulses formed characteristically with respect to the chronological amplitude curve thereof, and the frequency of which is between 1 and 1000 Hz. Such a primary pulse can be constructed in this case from a superposition of a base pulse rising or falling according to a power function with an array of superimposed pulses each of shorter duration and different form and chronological sequence.

The chronological amplitude curve of such a primary pulse could approximately correspond to the following function:

$$y(x) = \frac{x^a * k * e^{\sin x^b}}{c} + d$$

therein:
y(x)=denotes magnetic field amplitude within the primary pulse as a function of x;
x=denotes the time curve, wherein x begins again with the same initial value for each primary pulse;
a=denotes a parameter for setting the chronological amplitude curve of each primary pulse (envelope curve);
b=denotes the number of the subpulses;
c=denotes a factor for setting the amplitude;
d=denotes an offset value;
where a, b, c≠0.

The parameter a is in this case in a range from 0.1 to 50, preferably in a range from 0.5 to 10, and particularly preferably in a range from 1 to 5. The parameter b is in this case in a range from 0.5 to 50, preferably in a range from 1 to 10, and particularly preferably in a range from 2 to 5.

In the meaning of this patent specification, above-mentioned function (1) is understood as a function which is capable of describing a corresponding amplitude curve, but describes the amplitude curve with the aid of other functions or function components in relation to the illustrated function. These are in particular those functions which contain trigonometric functions, for example, sin x, cos x, arc sin x, or arc cos x. These functions or partial functions can replace individual components of the formula.

The device is designed for this purpose such that a rest phase is provided between two successive pulse groups of the primary pulses. It has been shown that, presumably because of the relaxation time of the exchange processes, such a rest phase has a positive effect on the molecular mechanisms within the treated body tissue and thus displays better therapy success. The molecular processes can substantially resume the normal function thereof during the rest phase. This rest phase is designed according to the Invention such that the curve of the maximum amplitude of the primary pulses at the beginning of the rest phase has a slope m in the range from −∞<m<0.1 and/or at the end of the rest phase has a slope m from ∞>m>0.1. The amplitudes of the primary pulses drop very strongly at the beginning of the pause to rapidly reduce the biological effect of the electromagnetic pulses and rapidly achieve the relaxation of the molecular processes. In order that the activation of the molecular processes begins rapidly again at the end of the rest phase, the maximum amplitude of the primary pulses rises steeply at the end of the rest phase.

In a further embodiment of the invention, the reduction of the maximum amplitude of the primary pulses in the region of the rest phase is at least 40%, preferably 25%, and particularly preferably 15% of the maximum amplitude of the pulse group before the beginning and/or after the end of the rest phase. The activation of the molecular processes in the treated body tissue is thus not completely switched off during the rest phase, but rather is continued with significantly lower intensity. The stimulation, for example, of the vasomotor system of small and ultrasmall blood vessels is therefore maintained and thus enables more favorable blood flow in the treated body tissue.

In a further aspect of the Invention, the duration of the rest phase is at least 0.1 seconds, preferably 1 second, and particularly preferably 3 seconds. It has been shown that the molecular exchange processes presumably relax sufficiently during this time span and can substantially resume the normal function thereof. During this rest phase, as described above, the reduction of the maximum amplitude of the primary pulses is at least 40%, preferably 25%, and particularly preferably 15% of the maximum amplitude of the pulse group before the beginning and/or after the end of the rest phase.

In a further embodiment of the invention, the maximum amplitude of the primary pulses extends in a constant manner in the region of the rest phase. Variations of the maximum amplitudes of the primary pulses are avoided during the rest phase to keep the activation of molecular mechanisms at a lower level.

It has been shown that lowering the maximum amplitude of the primary pulses excessively rapidly at the beginning of the rest phase Interferes with the course of therapy, presumably because the different molecular processes also relax differently. In one particular embodiment, the subsiding duration of the maximum amplitude of the primary pulses at the beginning of the rest pause is between ¼ and ⅓ of the total duration of the rest phase. It is thus ensured that all molecular mechanisms are substantially deactivated by the electromagnetic signal during the rest phase.

In a refining form of the invention, the rising duration of the maximum amplitude of the primary pulses at the end of the rest phase is between ¼ and ¾ of the total duration of the rest phase. This process causes a uniform excitation, which is gentler for the patient, of the molecular mechanisms in the treated tissue.

In a further embodiment of the invention, the ratio of the mean slope of the curve of the maximum amplitude of the primary pulse at the beginning of the rest phase mB and the mean slope of the curve of the maximum amplitude of the primary pulse at the end of the rest phase mE Is, according to the invention, between −1>mB/mE>−10, i.e., at the end of the rest phase the maximum amplitude of the primary pulse rises equally or less by the cited factors than the primary pulse subsides at the beginning of the rest phase. Experience has shown that the excitation at the end of the rest phase should rise less than the excitation subsides at the beginning of the rest phase. It is thus ensured that, on the one hand, all molecular processes are no longer excited uniformly at the beginning of the rest phase. On the other hand, the excitation at the end of the rest phase takes place more gently for the patient and thus displays better therapy success.

A frequency change of the frequency of the primary pulse of a pulse group takes place during the rest phase in a special embodiment of the invention. According to the invention, the value of the frequency of the primary pulse of a pulse group before the rest phase has a different value than the value of the frequency of the primary pulse of a pulse group after the rest phase. The intensity distribution of the pulses over time thus changes after the rest phase. The electromagnetically induced activation acts on different molecular mechanisms after the rest phase than before the rest phase. A broader excitation, activation of the processes, and a better therapy success are thus achieved by this frequency change according to the invention.

BRIEF DESCRIPTION OF THE DRAWING

The invention will be explained in greater detail on the basis of the drawing. In the figures:

FIG. 2 a) shows subpulses of a primary pulse, b) shows a primary pulse composed of subpulses, c) shows a simplified Illustration of a primary pulse.

DETAILED DESCRIPTION OF PREFERRED EMBODIMENTS

Figure 1:
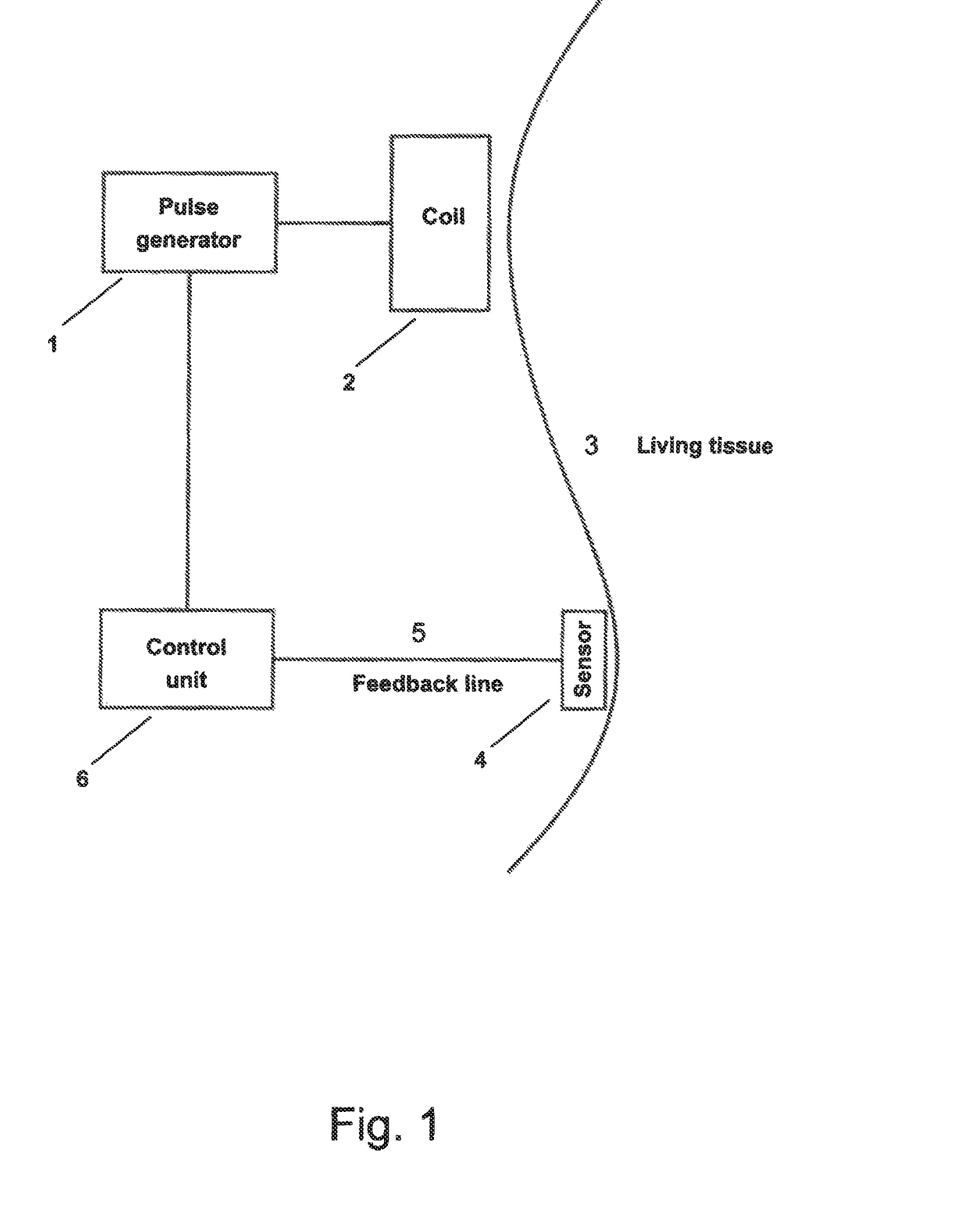
FIG. 1 shows a device according to the invention.

In detail, FIG. 1 shows a device according to the invention, which comprises at least one pulse generator 1, which generates a pulsating magnetic field in the coil 2. The field interacts with the living tissue 3, in particular a body of a patient to be treated. Furthermore, the device according to the invention comprises a sensor, using which physical parameters, for example, the temperature, the blood pressure, the heart rate, or the oxygen content of the blood can be detected. The detected physical parameters are transmitted to a control unit 6 via the feedback line 5. The detected physical parameters can be analyzed and the pulsating magnetic field can be optimized in the generator 1 via the parameters and corresponding algorithms. It is possible to detect and optimize multiple parameters at the same time, in order to set an effective pulsating magnetic field. The control unit 6 can also automatically establish the optimum values for each of the parameters a to d and k as a function of these effects.

Furthermore, the effect of the pulsating magnetic field on the body to be treated can be detected via the sensor 4 and various parameters of the magnetic field can be set in dependence thereon. Such parameters are, for example, the frequency of individual, primary, and secondary pulses and/or subpulses or the amplitude of these pulses. The control unit determines the proportion transmitted to the body to be treated from the differences, in particular in the spectral composition between the field energy generated by the field generation and the magnetic field detected by the sensor. The parameters of the pulsating magnetic field (a to d and k) can be adapted and optimized with respect to the treatment effect via the control unit.

Figure 2:
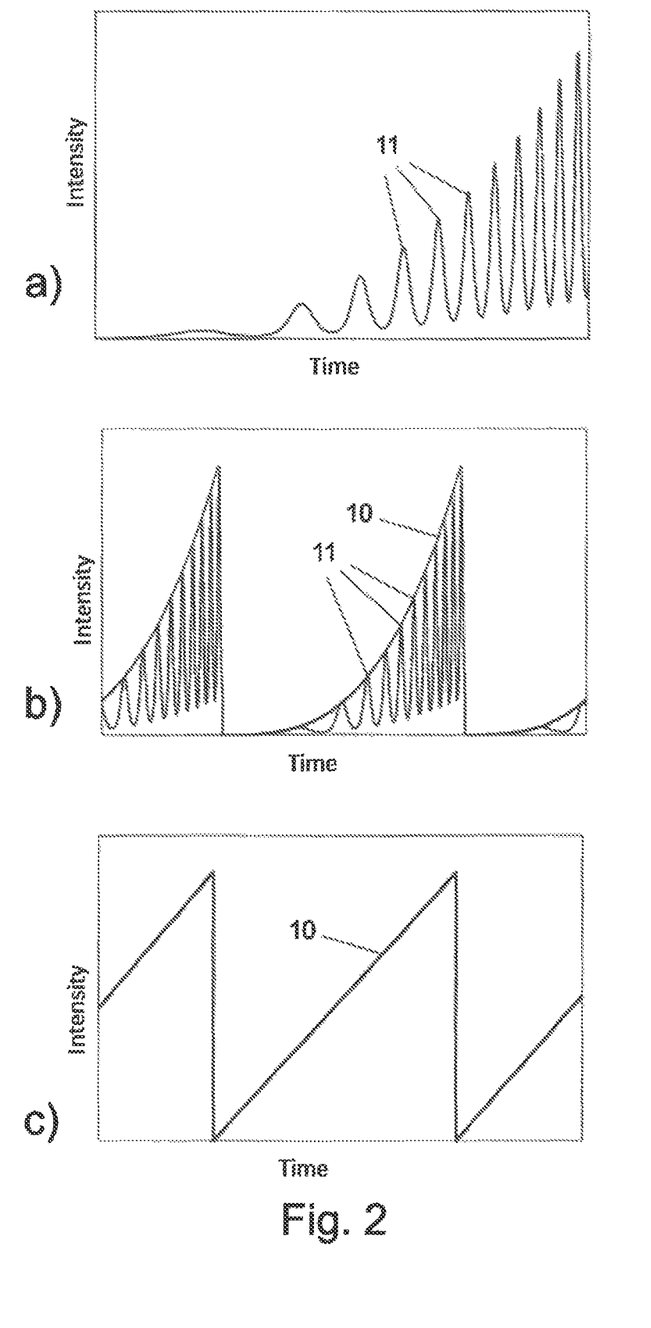

A pulsating magnetic field is generated with the aid of the device according to the invention and the method according to the invention. The magnetic field has a sequence of primary pulses 10, the curve of which corresponds in principle with respect to amplitude and time to the curve shown in FIG. 2b. A simplified form of the amplitude curve is shown in FIG. 2c. The shape of the amplitude curves is dependent on the parameters a to d. Each primary pulse 10 is composed in this case of a sequence of subpulses 11. The maximum Intensities of the subpulses 11 rise in the course of a primary pulse 10.

The primary pulses 10, from which the pulsed magnetic field is composed, begin at a time t1 and reach the mean minimum or maximum value thereof. The mean amplitude of the primary pulse 10, and/or the periodically modulated amplitudes therein, rise or fall on average in the course of each primary pulse 10. Increase or decrease takes place according to an exponential function. However, other functions are also conceivable, which describe the mean rise (drop) of the amplitude of a primary pulse 10 within the time. The optimum shape of the sequence of the subpulses 11 is very different individually. It depends on the type of the tissue to which the field is applied, the desired healing success, and the respective individual.

A short "rest time" of specific length can be located between the primary pulses 10, which is presumably required as a result of the relaxation time of the exchange processes and experience has shown leads to better excitation of the living body tissue. The duty cycle between rest time and active pulse time can vary between 3:1 to 1:3 and is preferably approximately 1:1. It is in the order of magnitude of 0 to 200 ms, for example. The duty cycle between rest time (times ta to tb) and pulse repetition duration T is preferably between 0% and 300%. However, in some applications the rest phase can be omitted.

Figure 3:
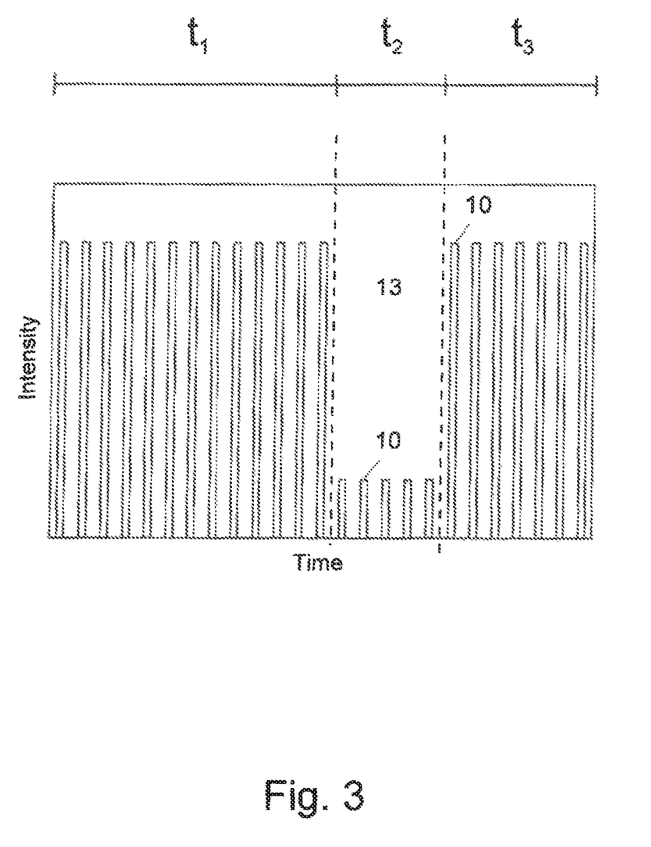
FIG. 3 shows primary pulses interrupted by a rest pulse with uniform amplitude during the rest phase.

Furthermore, the sequence of a plurality of the primary pulses 10 can be separated by rest phases 13, cf. FIG. 3. These rest phases 13 have a duration (tB in FIG. 5) of a plurality of primary pulses 10, which is at least greater than 10 primary pulses. The duration of the rest phase 13 tB is preferably greater than 0.5 seconds, particularly preferably greater than 2 seconds. During these rest phases 13, the average maximum amplitude I of the primary pulses 10 is reduced to less than or equal to 30% of the maximum amplitude of the primary pulses in tA. A reduction to 0 is also possible. The tissue to which the pulses are applied is given the opportunity for regeneration and relaxation in this rest phase 13.

Figure 4:
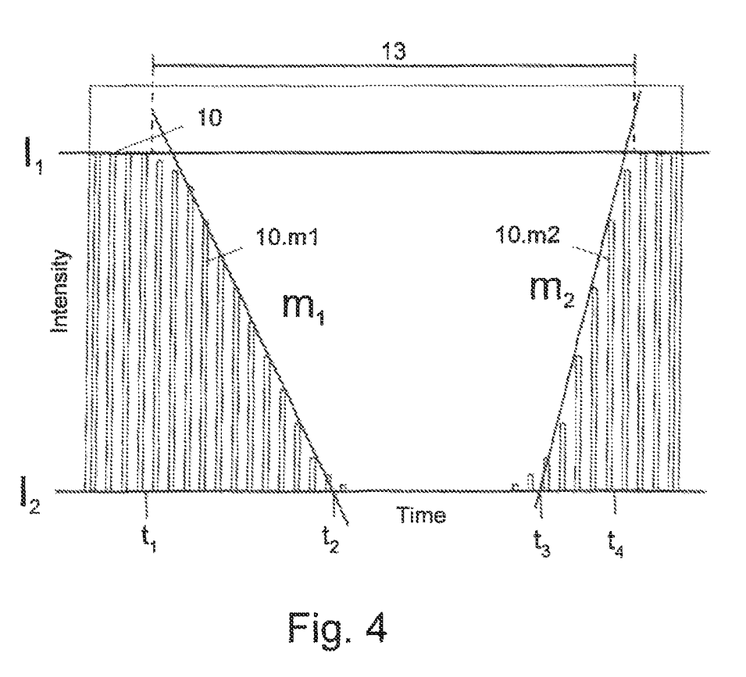
FIG. 4 shows primary pulses interrupted by a rest phase with amplitude curves of different slopes at the beginning and end of the rest phase.

FIG. 4 shows an exemplary embodiment according to the invention of an embodiment of the rest pause 13. Firstly a sequence of primary pulses 10 is provided, which have a constant maximum amplitude I. At the time $t_1$, the maximum amplitude I of the primary pulses 10 begins to decrease continuously until, at a time $t_2$, a minimum of the maximum amplitude I of the primary pulses 10 is reached. In the time Interval between $t_1$ and $t_2$, the mean slope mB of the maximum amplitude I has a value of mB=−0.12. A time interval follows between $t_2$ and $t_3$, in which the reduced maximum amplitude I of the primary pulses 10 is equal to 0. The time interval between $t_2$ and $t_3$ is 0.12 seconds long. A rest phase then follows between $t_3$ and $t_4$, in which the maximum amplitude I increases again. The mean slope mE is mE=0.12 here. After $t_4$, the maximum amplitude I of the primary pulses 10 is again at the same value as before $t_1$.

In a similar embodiment of the invention (not shown in the figure) the maximum amplitude I of the primary pulses 10 increases after $t_4$ to a 20% higher value than the maximum amplitude I of the primary pulses 10 before $t_1$. During the interval between $t_2$ and $t_3$, the maximum amplitude I of the primary pulses 10 is constant at 5% of the maximum amplitude I of the primary pulses 10 before $t_1$.

Figure 5:
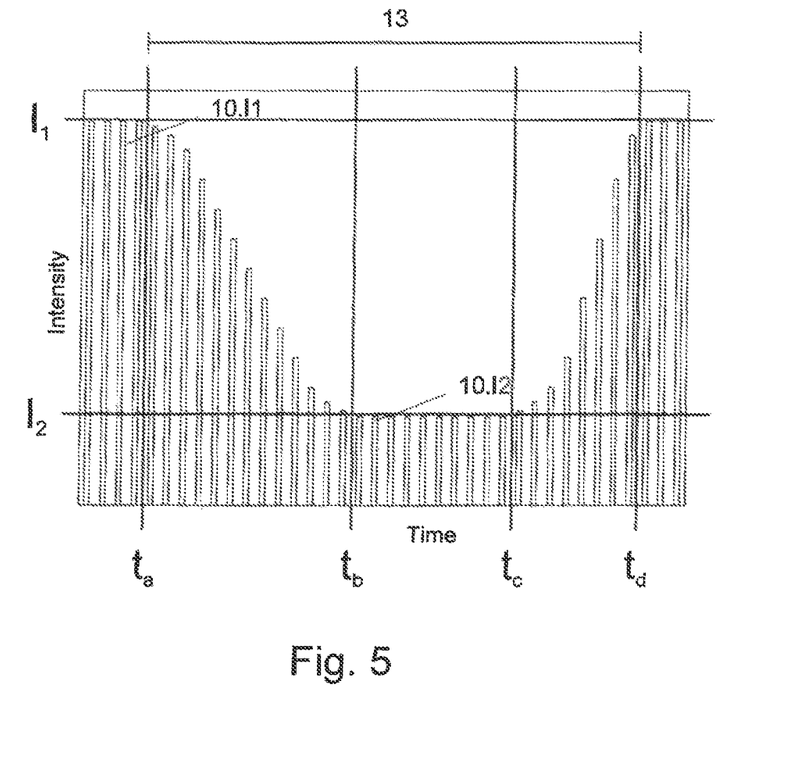
FIG. 5 shows primary pulses interrupted by a rest phase with uniform amplitude during the rest phase and amplitude curves of different slopes at the beginning and end of the rest phase.

A further exemplary embodiment of the invention is shown in FIG. 5. After a first sequence of primary pulses 10 with constant maximum amplitude I, the rest phase 13 begins from $t_1$. It has a total of three regions, a first from $t_1$ to $t_2$, in which the maximum amplitude I is reduced, a second region from $t_2$ to $t_3$, in which the maximum amplitude I of the primary pulses 10 is constant at 30% of the maximum amplitude I of the first sequence of the primary pulses 10, and a third region between $t_3$ and $t_4$, in which the maximum amplitude I of the primary pulses 10 rises again. After $t_4$, the maximum amplitudes I of the primary pulses 10 have the same values as before $t_1$. While the mean slope m during the reduction of the maximum amplitude I during the first phase of the rest phase 13 is at mB=−2, in the third phase of the rest phase 13 it has a value of mE=3. The ratio of the mean slope of the first phase of the rest phase 13 to the mean slope of the third phase of the rest phase 13 is therefore at mB/mE=−⅔. The second phase of the rest phase 13 is 1.2 seconds long.

Figure 6:
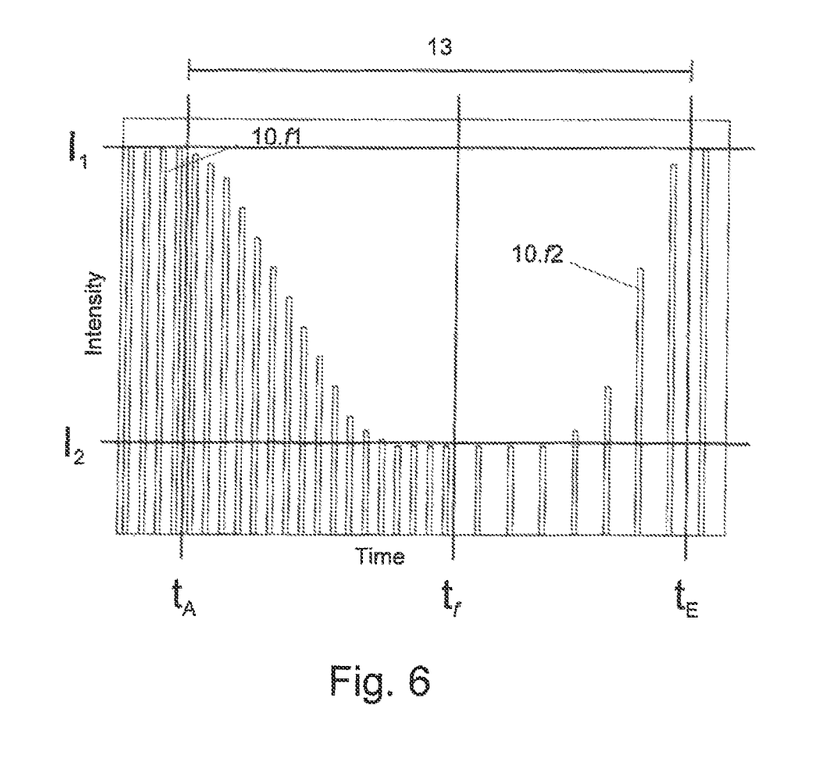
FIG. 6 shows primary pulses interrupted by a rest phase with uniform amplitude during the rest phase and amplitude curves of different slopes at the beginning and end of the rest phase.

In a further advantageous embodiment of the invention, the maximum amplitude I of the primary pulses 10 is reduced for a longer second phase to a constant level of 20% of the maximum amplitude I of the primary pulses 10 before $t_1$ (FIG. 6). The second phase is 3.6 seconds here. However, it is also shown here that the embodiment of the first phase and the third phase of the rest phase 13 have a decisive Influence on the stimulation of the physiological exchange processes. The mean slope mB of the maximum amplitude I of the primary pulses 10 in the first phase of the rest phase 13 from $t_1$ to $t_2$ is mB=−1 here, while the mean slope mE have the maximum amplitude I of the primary pulses 10 in the second phase of the rest phase 13 from $t_2$ to $t_3$ is mE=0.8. During the second phase of the rest phase 13 between $t_2$ and $t_3$, the frequency was reduced from f=30 Hz to f=10 Hz at the time $t_f$.

In addition to other effects, the Individual embodiment of the rest phase 13 results in a stimulation of the physiological exchange processes and thus contributes decisively to accelerating the claimed regulation and healing processes. It is important in particular in this case that due to the embodiment of the introduction of the rest phase and the further increase of the pulses, the relaxation of the processes in the body tissue already stimulated by electromagnetic application has a decisive influence on the overall effect. This rest phase and the individually adapted embodiment thereof forms the essential difference here from EP 0 995 403 B1 and EP 2 050 481 A1.

Not only the optimum shape and sequence of the primary pulses 10 are dependent on the type of the tissue to which the field is applied, the desired healing success, and the respective individual and therefore individually differ greatly, but rather also the manner in which the tissue is guided into the relaxation phase. Moreover, it has been shown that the molecular exchange processes presumably relax sufficiently during the rest phase and can substantially resume the normal function thereof.

If specific parameters of the living tissue, in particular of the human body, are detected with the aid of sensors, in addition the curve of each resulting primary pulse 10 may be adapted to the actual conditions such that an optimum stimulation is achieved, also the rest phases 13 and the embodiment thereof have substantial influence thereon and are to be individually adapted. For this purpose, the level of the maximum amplitude of the primary pulses 10 during the rest phase 13, the mean slope of the maximum amplitude at the beginning and the end of the rest phase 13, and the duration thereof are set in dependence on the detected tissue parameters such that application and relaxation are in a ratio optimized for this tissue.

A further optimization of the effect of the present device on the organism can be achieved by feedback. For this purpose, sensors are used, which measure one or more physical parameters around the surroundings of the application, to detect the excitation of the organism by the electromagnetic pulses. Tissue parameters, for example, blood pressure, temperature, pulse, pH value, or respiratory volume may be measured using the sensors and may be used in the sense of an adaptive adaptation of the stimulation to the sensitivity of the tissue to be stimulated to optimize the parameters of the device for generating electromagnetic fields. In particular, the adaptation may be performed dynamically during the treatment, to thus take into consideration short-term changes of the physical state and further optimize the treatment success. This takes place via a feedback loop by which the sensitivity changes in the impinged tissue caused by the excitation itself can be compensated for.

The invention claimed is:

1. A device for influencing biological processes in living tissue, comprising:
    a field generation device configured for generating a pulsating magnetic field,
    a pulse generator configured for controlling the field generation device so as to apply to at least a part of the living tissue, the pulsating magnetic field composed of a sequence of primary pulses having a pulse repetition rate of between 0.01 and 1000 Hz, wherein the primary pulses are formed of a plurality of superimposed sub-pulses, with an amplitude curve of a primary pulse defined by equation (1):

$$y(x) = \frac{x^a * k * e^{sinx^b}}{c} + d \quad (1)$$

wherein:
x denotes a time;
y(x)=denotes a magnetic field amplitude within the primary pulse as a function of time x; wherein each primary pulse has an identical initial value at a start time;
a=denotes a parameter for setting an envelope curve of the magnetic field amplitude within each primary pulse;
b=denotes a number of the sub-pulses;
c=denotes an amplitude scaling factor;
d=denotes an offset value;
k=denotes an amplitude scaling factor for the sub-pulses, with a, b, c not equal to 0;
wherein the primary pulses are combined into pulse groups with a respective rest phase disposed between two successive pulse groups,
wherein a curve profile of a maximum amplitude of the primary pulses at a beginning of a respective rest phase has a slope mB of −∞<mB<−0.1 and/or at an end of the respective rest phase has a slope mE of −∞>mE>0.1, both slopes in units of milli-Tesla/second (mT/s); and
wherein a ratio of a mean slope mB of the curve profile of the maximum amplitude of the primary pulse at the beginning of the rest phase and a mean slope mE of the curve profile of the maximum amplitude of the primary pulse at the end of the rest phase has a value −1>mB/mE>−10.

2. The device of claim 1, wherein a maximum amplitude of the primary pulses in a region of the rest phase is reduced to at least 40% of a maximum amplitude of a pulse group before the beginning and/or after the end of the rest phase.

3. The device of claim 1, wherein a maximum amplitude of the primary pulses in a region of the rest phase is reduced to 25% of a maximum amplitude of a pulse group before the beginning and/or after the end of the rest phase.

4. The device of claim 1, wherein a maximum amplitude of the primary pulses in a region of the rest phase is reduced to 15% of a maximum amplitude of a pulse group before the beginning and/or after the end of the rest phase.

5. The device of claim 1, wherein the rest phase lasts at least 0.1 seconds.

6. The device of claim 1, wherein the rest phase lasts 1 second.

7. The device of claim 1, wherein the rest phase pasts 3 seconds.

8. The device of claim 1, wherein a curve profile of a maximum amplitude of the primary pulses remains constant in the region of the rest phase.

9. The device of claim 1, wherein a duration of a decrease of the maximum amplitude of the primary pulses at the beginning of the rest phase is between ⅓ and ¼ of a total duration of the rest phase.

10. The device of claim 1, wherein a duration of an increase of the maximum amplitude of the primary pulses at the end of the rest phase is between ¾ and ¼ of a total duration of the rest phase.

11. The device of claim 1, wherein a frequency of the primary pulse of a pulse group before the rest phase is changed to the frequency of a pulse group after the rest phase during the rest phase.

12. The device of claim 1, wherein the living tissue is a human body.

* * * * *

UNITED STATES PATENT AND TRADEMARK OFFICE
CERTIFICATE OF CORRECTION

PATENT NO. : 11,090,504 B2
APPLICATION NO. : 16/463734
DATED : August 17, 2021
INVENTOR(S) : Peter Gleim It is certified that error appears in the above-identified patent and that said Letters Patent is hereby corrected as shown below:

On the Title Page

Page 2, Under OTHER PUBLICATIONS

Column 1, Line 11, non-patent literature by R. Klopp:
Replace "Bermer 3000" with --BEMER 3000--.

Column 1, Line 22:
Replace "lurch" with --durch--,

Column 1, Lines 23-24:
Replace "LED-Licht-Thorapie" with --LED-Licht-Therapie--, Column 2, Line 2:
Replace "Kleinitertage" with --Kleintiertage--.

Column 2, Line 6:
Replace "Medicine Soartiva" with --Medicina Sportiva--.

Column 2, Line 21:
Replace "electromaenetic" with --electromagnetic--.

Column 2, Line 32:
Replace "Schlafqualitat" with --Schlafqualität--.

Column 2, Line 50:
Replace "%" with --&--.

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*